United States Patent
Marka et al.

(10) Patent No.: US 8,888,696 B2
(45) Date of Patent: Nov. 18, 2014

(54) SURGICAL LAMP WITH SUSPENSION SYSTEM

(75) Inventors: Rudolf Marka, Ismaning (DE); Michael Schmid, Groebenzell (DE); Fred Held, Hamburg (DE)

(73) Assignee: Trumpf Medizin Systeme GmbH + Co. KG, Saalfeld (DE)

(*) Notice: Subject to any disclaimer, the term of this patent is extended or adjusted under 35 U.S.C. 154(b) by 237 days.

(21) Appl. No.: 12/487,105

(22) Filed: Jun. 18, 2009

(65) Prior Publication Data

US 2009/0318770 A1 Dec. 24, 2009

(30) Foreign Application Priority Data

Jun. 20, 2008 (EP) .................................... 08011293

(51) Int. Cl.
| | |
|---|---|
| A61B 1/06 | (2006.01) |
| F21S 4/00 | (2006.01) |
| F21V 19/02 | (2006.01) |
| F21V 21/00 | (2006.01) |
| A61B 19/00 | (2006.01) |
| F21V 21/28 | (2006.01) |
| F21V 21/30 | (2006.01) |
| F21W 131/205 | (2006.01) |

(52) U.S. Cl.
CPC ............. *A61B 19/5202* (2013.01); *F21V 21/28* (2013.01); *F21V 21/30* (2013.01); *F21W 2131/205* (2013.01)
USPC ....... 600/249; 362/572; 362/220; 362/249.11

(58) Field of Classification Search
CPC ...... F21V 21/403; F21V 7/0025; F21V 21/28
USPC ......... 362/469, 403, 413, 419, 427, 431, 275, 362/287, 572, 573, 576, 220, 249.1, 249.11, 362/282, 322, 432; 600/249
See application file for complete search history.

(56) References Cited

U.S. PATENT DOCUMENTS

| | | | | |
|---|---|---|---|---|
| 1,412,544 | A | * | 4/1922 | Shirreffs ..................... 248/278.1 |
| 1,708,047 | A | * | 4/1929 | Bosworth ..................... 362/427 |
| 1,864,756 | A | * | 6/1932 | Pieper ........................... 248/568 |
| 2,896,066 | A | * | 7/1959 | Quetin ............................ 362/33 |
| 3,005,087 | A | * | 10/1961 | Klein ............................. 362/33 |
| 3,191,023 | A | * | 6/1965 | Jones et al. ................... 362/220 |
| 3,437,803 | A | * | 4/1969 | Schafer et al. ................... 362/8 |

(Continued)

FOREIGN PATENT DOCUMENTS

| | | |
|---|---|---|
| DE | 3243709 | 5/1984 |
| DE | 29510274 | 10/1995 |

(Continued)

OTHER PUBLICATIONS

European Search Report for corresponding European Application No. EP 08011293, mailed Nov. 26, 2008, 4 pages.

*Primary Examiner* — Ellen C Hammond
*Assistant Examiner* — Jacqueline Johanas
(74) *Attorney, Agent, or Firm* — Fish & Richardson P.C.

(57) ABSTRACT

A surgical lamp that includes a lamp body having a central axis, and a suspension system for connecting the lamp body with a carrying system. The suspension system can include a first pivot joint around a first pivot axis that is perpendicular to the central axis, and the first pivot joint can be located in the central region of the lamp body.

12 Claims, 4 Drawing Sheets

(56) References Cited

U.S. PATENT DOCUMENTS

| | | | |
|---|---|---|---|
| 3,786,244 A * | 1/1974 | Hutter, III | 362/33 |
| 3,887,801 A * | 6/1975 | Ilzig et al. | 362/33 |
| 4,025,778 A * | 5/1977 | Hayakawa | 362/233 |
| 4,280,167 A * | 7/1981 | Ellett | 362/33 |
| 4,380,790 A * | 4/1983 | Saferstein et al. | 362/231 |
| 4,395,750 A * | 7/1983 | Scheidemann et al. | 362/239 |
| 4,501,557 A * | 2/1985 | Tamura et al. | 433/79 |
| 4,517,632 A * | 5/1985 | Roos | 362/389 |
| 4,527,225 A * | 7/1985 | Hartman | 362/294 |
| 4,581,689 A * | 4/1986 | Oram | 362/275 |
| 4,608,622 A * | 8/1986 | Gonser | 362/573 |
| 4,722,502 A * | 2/1988 | Mueller et al. | 248/284.1 |
| 4,744,019 A * | 5/1988 | Krogsrud | 362/402 |
| 4,803,607 A * | 2/1989 | Jonsson | 362/249.07 |
| 4,967,320 A * | 10/1990 | Paschal | 362/96 |
| D312,140 S * | 11/1990 | Jonsson | D26/63 |
| D315,801 S * | 3/1991 | Luger | D26/24 |
| 5,025,359 A * | 6/1991 | Saluja et al. | 362/402 |
| 5,038,261 A * | 8/1991 | Kloos | 362/286 |
| 5,424,931 A * | 6/1995 | Wheeler | 362/418 |
| 5,473,524 A * | 12/1995 | Behringer | 362/294 |
| 5,477,443 A * | 12/1995 | Cvek | 362/413 |
| 5,497,295 A * | 3/1996 | Gehly | 362/581 |
| 5,539,626 A * | 7/1996 | Scholz | 362/237 |
| 5,595,441 A * | 1/1997 | McGee | 362/473 |
| 5,803,905 A * | 9/1998 | Allred et al. | 600/249 |
| 5,808,680 A | 9/1998 | Steckhan | |
| 6,019,484 A * | 2/2000 | Seyler | 362/287 |
| 6,290,645 B1 * | 9/2001 | Goldfarb et al. | 600/249 |
| 6,416,207 B1 * | 7/2002 | Chang | 362/419 |
| 6,431,515 B1 * | 8/2002 | Gampe et al. | 248/324 |
| 6,439,748 B1 * | 8/2002 | Hsieh | 362/360 |
| 6,450,671 B1 | 9/2002 | Scholz et al. | |
| 6,513,962 B1 * | 2/2003 | Mayshack et al. | 362/583 |
| 6,633,328 B1 * | 10/2003 | Byrd et al. | 348/143 |
| 6,639,623 B2 * | 10/2003 | Howell et al. | 348/61 |
| 6,793,380 B2 * | 9/2004 | Kupfer | 362/371 |
| 7,131,752 B2 * | 11/2006 | Beveridge et al. | 362/397 |
| 7,131,753 B1 * | 11/2006 | Edwards, Jr. | 362/405 |
| 7,397,384 B1 * | 7/2008 | MacKenzie et al. | 340/638 |
| 7,465,065 B2 * | 12/2008 | Marka | 362/232 |
| 7,665,875 B2 * | 2/2010 | Whitman | 362/572 |
| 7,682,042 B2 * | 3/2010 | Feinbloom et al. | 362/249.03 |
| 7,746,009 B2 * | 6/2010 | Held et al. | 315/362 |
| 7,810,948 B2 * | 10/2010 | Ogashiwa | 362/239 |
| 7,980,738 B2 * | 7/2011 | Chiang | 362/427 |
| 8,454,197 B2 * | 6/2013 | Hauschulte et al. | 362/249.03 |
| 2003/0021107 A1 * | 1/2003 | Howell et al. | 362/147 |
| 2005/0195599 A1 * | 9/2005 | Marka | 362/232 |
| 2006/0082997 A1 * | 4/2006 | Derrien et al. | 362/236 |
| 2006/0104069 A1 * | 5/2006 | Beveridge et al. | 362/397 |
| 2006/0291204 A1 * | 12/2006 | Marka et al. | 362/239 |
| 2007/0014567 A1 | 1/2007 | Rossner et al. | |
| 2007/0030702 A1 * | 2/2007 | Held et al. | 362/647 |
| 2007/0041167 A1 * | 2/2007 | Nachi | 362/33 |
| 2009/0316394 A1 * | 12/2009 | Fritze et al. | 362/231 |
| 2009/0318770 A1 * | 12/2009 | Marka et al. | 600/249 |
| 2009/0318771 A1 * | 12/2009 | Marka et al. | 600/249 |
| 2009/0318772 A1 * | 12/2009 | Marka et al. | 600/249 |

FOREIGN PATENT DOCUMENTS

| | | |
|---|---|---|
| DE | 29510724 | 10/1995 |
| EP | 0121414 | 10/1984 |
| EP | 1016820 | 12/1999 |
| EP | 1087176 | 9/2000 |
| EP | 1728482 | 5/2005 |
| JP | 08038505 | 2/1996 |

* cited by examiner

SURGICAL LAMP WITH SUSPENSION SYSTEM

CROSS REFERENCE TO RELATED APPLICATION

This application claims priority under 35 U.S.C. §119(a) to European Patent Application No. 08 011 293.1, filed Jun. 20, 2008, the entire contents of which are hereby incorporated by reference.

TECHNICAL FIELD

The invention concerns a surgical lamp with a suspension system.

BACKGROUND

Surgical lamps are typically attached to a room ceiling or wall, or a mobile stand by means of a so-called carrying system. Usually, the carrying system includes a first boom that is pivotable around a vertical axis, and a second boom that is horizontally pivotable and height-adjustable. It is possible to position the surgical lamp at a location in the room, where it is advantageous to illuminate the operation site.

An articulated suspension system allows the orientation of the surgical lamp and consequently the direction of the emitted light in the three rotatory degrees of freedom. In a simple version, the suspension system usually consists of a yoke approximately having the shape of a circular arc extending to a quadrant (quarter yoke), which is pivotable around a first vertical axis at its upper end, located at the outer end of the second boom of the carrying system. Also at the lower end of the yoke, a pivot joint is located, at which the lamp body of the surgical lamp is laterally attached, pivotably around a second horizontal axis (semi cardanic suspension). However, it is not possible to directly adjust certain light directions because the lamp body is merely pivotable around the horizontal axis. For adjusting certain light directions, the suspension system must first be pivoted around the vertical axis.

A second yoke (comfort yoke), which also includes a shape of a circular arc and extends to a quadrant, was introduced to remedy this disadvantage and to permit handling of the surgical lamp in a more comfortable way. The diameter of the second yoke is smaller than the diameter of the first yoke and both yokes are concentrically arranged around the virtual center of the first yoke.

At its first end, the second yoke is rotatably joined to the first yoke in the second pivot axis, and, at its second end, the lamp body is laterally attached pivotably around a third pivot axis. Therefore, the suspension system has three pivot axes. The first and the second axis are perpendicular to one another, and the second and the third axis are perpendicular to one another. Hence, it is possible to orientate the lamp body in any desired direction with a pivot movement around the second and/or third axis. Thus, it is possible to determine the direction of the light emission, as requested (full cardanic suspension).

However, this arrangement requires a considerable expenditure because of the additional yoke. In addition, the body and yokes occupy more installation space, and, due to increased weight, the operating force is increased. Furthermore, the height of the suspension system increases about 5 cm to 8 cm because of the additional space requirement for spinning of the quarter yoke below the vertical pivot joint. Thus, the head room below the lamp head is reduced.

Furthermore, the quarter yoke is exposed to high strain because of torque and torsion, respectively. Therefore, it is difficult to cause the two axes, which are offset by 90°, to traverse in the center of gravity of the lamp head (vertical offset). The angle deviation of the axes from the 90° angle, which is generated by the quarter circular shape of the quarter yoke, is a further problem because both pivot axes do not pass through the center of gravity of the lamp body (horizontal offset). Hence, it is necessary to keep pre-adjusted positions of the lamp head by strongly adjusted breaks which increase the operation force.

In some systems, a yoke having the shape of a half circular arc is pivotably arranged around its longitudinal axis, the yoke encompasses the lamp body, and the lamp body is pivotably mounted at both ends of the yoke. In this case, the second pivot axis is arranged in the space in an inclined manner, which increases the difficulty level of operation, and the lamp body cannot be pivoted around its center axis, which leads to problems in operation of the surgical lamp, particularly if the operating elements are arranged at the circumference of the lamp head. This way of operation is similar to the operation of a semi cardanic suspension.

SUMMARY

In one aspect of the invention, a surgical lamp includes a lamp body having a central axis, a carrying system, and a suspension system connecting the lamp body to the carrying system. The suspension system includes at least first and second pivot joints. The first pivot joint is connected to the lamp body in a central area of the lamp body and has a first pivot axis that is perpendicular to the central axis. The lamp body is pivotable around the first pivot axis.

In some embodiments, the second pivot joint has a second pivot axis that is perpendicular to the first pivot axis.

In certain embodiments, the first pivot axis and the second pivot axis intersect at a center of gravity of the lamp body.

In some embodiments, the suspension system includes a first connection element between the first pivot joint and the second pivot joint, and the first connection element is configured such that the lamp body can freely rotate relative to the first connection element.

In certain embodiments, the lamp body defines a recess sized to receive the first connection element of the suspension system when the lamp body is rotated relative to the first connection element.

In some embodiments, the lamp body comprises first and second members that are connected to one another via the first pivot joint, and the first and second members of the lamp body cooperate to define the recess.

In certain embodiments, the first pivot joint is a universal joint, and the suspension system further includes a connection element disposed between the universal joint and the second pivot joint.

In some embodiments, the connection element has a linear shape.

In certain embodiments, the suspension system further includes a third pivot joint having a third pivot axis that is vertically orientated and forms a maximum angle of 90° with the second pivot axis.

In some embodiments, the suspension system further includes a second connection element between the second pivot joint and the third pivot joint, the second connection element being configured to allow the lamp body to rotate.

In certain embodiments, the second connection element is arc-shaped.

In some embodiments, the second connection element includes at least of two portions arranged at an angle of less than 180° relative to one another.

In certain embodiments, the first pivot joint includes an adjusting mechanism that is adjustable in a direction along and parallel to the central axis of the lamp body.

In some embodiments, the first pivot joint includes an adjusting mechanism that is adjustable in a direction along and parallel to the first pivot axis.

In certain embodiments, the first pivot joint includes an adjusting mechanism that is adjustable in a direction that is perpendicular to the first pivot axis and perpendicular to the central axis of the lamp body.

According to another aspect of the invention, a surgical lamp is connected to a carrying system via a suspension system with at least two pivot joints. The suspension system includes a first pivot joint having a first pivot axis that is perpendicular to a center axis of the lamp body in the central area of the lamp body, and the lamp body is pivotable around the first pivot joint.

The arrangement of the first pivot axis in the central area of the lamp body provides the advantage that a second yoke can be waived while maintaining the same operating comfort. Thereby, an expensive yoke between the first and second pivot joint is spared. Because the lamp body has to be pivotable in two axes without restriction of the pivot range, in the conventional case, it is necessary to provide a clearance for spinning the yoke that partly encompasses the lamp body. The diameter of the lamp body is thus effectively enlarged, which requires a downward displacement of the second pivot axis. As a result, the head room of the operation personal is reduced. Such downward displacement is not necessary when using the pivot axis in the central area.

In some embodiments, the suspension system includes a second pivot joint having a second pivot axis that is perpendicular to the first pivot axis. As a result, a simple operation is achieved because all of the rotations can simply be performed around a desired axis in the horizontal plane.

In certain embodiments, the first and second pivot axes can intersect in an intersection point that is located approximately in the center of gravity of the lamp head so that a constant operation force for pivoting the lamp head is enabled. When a larger distance between the intersection point and the center of gravity exists, a lever arm exists between the weight force which is applied in the center of gravity and the intersection point. As a result, the center of gravity has to be pivoted upwards against the applied weight force or the applied weight force assists the downwards pivot movement of the center of gravity of the lamp body. Apart from that, there is a risk that the lamp body could move by itself. Thus, preadjusted positions of the lamp body have to be held by breaks that are strongly adjusted. This can increase the operation force.

In some embodiments, the surgical lamp includes a connection element having a length that, together with the dimensions of the pivot joints, allows a free spinning of the lamp head for enabling the spinning of the lamp body around the first and second pivot axes. This enables the lamp body to be adjusted to any of various desired space angle positions.

In certain embodiments, the suspension system of the surgical lamp includes a third pivot joint with a third pivot axis. The third pivot axis is oriented vertically and forms a maximum angle of 90° with the second pivot axis. This pivot axis allows the lamp body to be pivoted around a vertical axis and in this way to realize a desired space angle. The pivot axis further allows the lamp body to realize the desired space angle in any orientation of the third pivot axis of the surgical lamp.

An angle between the third vertical pivot axis and the second pivot axis, which is smaller than 90°, causes a rotational upward displacement of the second pivot joint around the intersection point of the first and second axis, which enlarges the head room of the surgical personal.

In some embodiments, the suspension system of the surgical lamp includes a second connection element between the second and third pivot joint. The shape of the second connection element can be selected to enable free spinning of the lamp body.

In certain embodiments, the connection element has the shape of an arc, or it includes two sections that form an angle that is smaller than 180°. This arrangement can reduce the amount of material and therefore reduce the masses to be moved.

In some embodiments, the suspension system of the surgical lamp includes a cardan joint (i.e., a universal joint) including the first and second pivot axis. The cardan joint is arranged in the central area of the lamp body. In this case, the random possibility for a free positioning is not possible but the operability is improved by reducing the masses to be moved because the connection element between the first and second pivot joint is omitted. In addition, the manufacturing expenses are further reduced.

In some embodiments, the suspension system of the surgical lamp including the cardan joint includes a third pivot joint with a third pivot axis, and a connection element between the cardan joint and third pivot joint. The connection element is designed in a linear shape, which further reduces the height and the masses to be moved.

In certain embodiments, the first pivot joint of the suspension system includes an adjusting mechanism that is adjustable in a direction of the center axis or in a direction parallel to the center axis. This allows for adjustments of the tolerances of the position of the center of gravity. This also permits the lamp body to be adjusted in such a way that the center of gravity is located at the intersection point of the first and second pivot axis.

In some embodiments, the first pivot joint of the suspension system includes an adjusting mechanism that is adjustable in a direction of the first pivot axis or in a direction parallel to the first pivot axis. This allows for adjustments to the tolerances of the position of the center of gravity. This also permits the lamp body to be adjusted in such a way that the center of gravity is located at the intersection point of the first and second pivot axis.

In certain embodiments, the first pivot joint of the suspension system includes an adjusting mechanism that is adjustable in a direction perpendicular to the center axis. This allows for adjustments to the tolerances of the position of the center of gravity. This also permits the lamp body to be adjusted in such a way that the center of gravity is located at the intersection point of the first and second pivot axis.

The surgical lamps described herein can advantageously include a suspension system that is reduced in expense and weight, has a reduced height, and provides a comfortable operation with reduced operation force.

Other aspects, features, and advantages are in the description, drawings, and claims.

DETAILED DESCRIPTION

Figure 1:
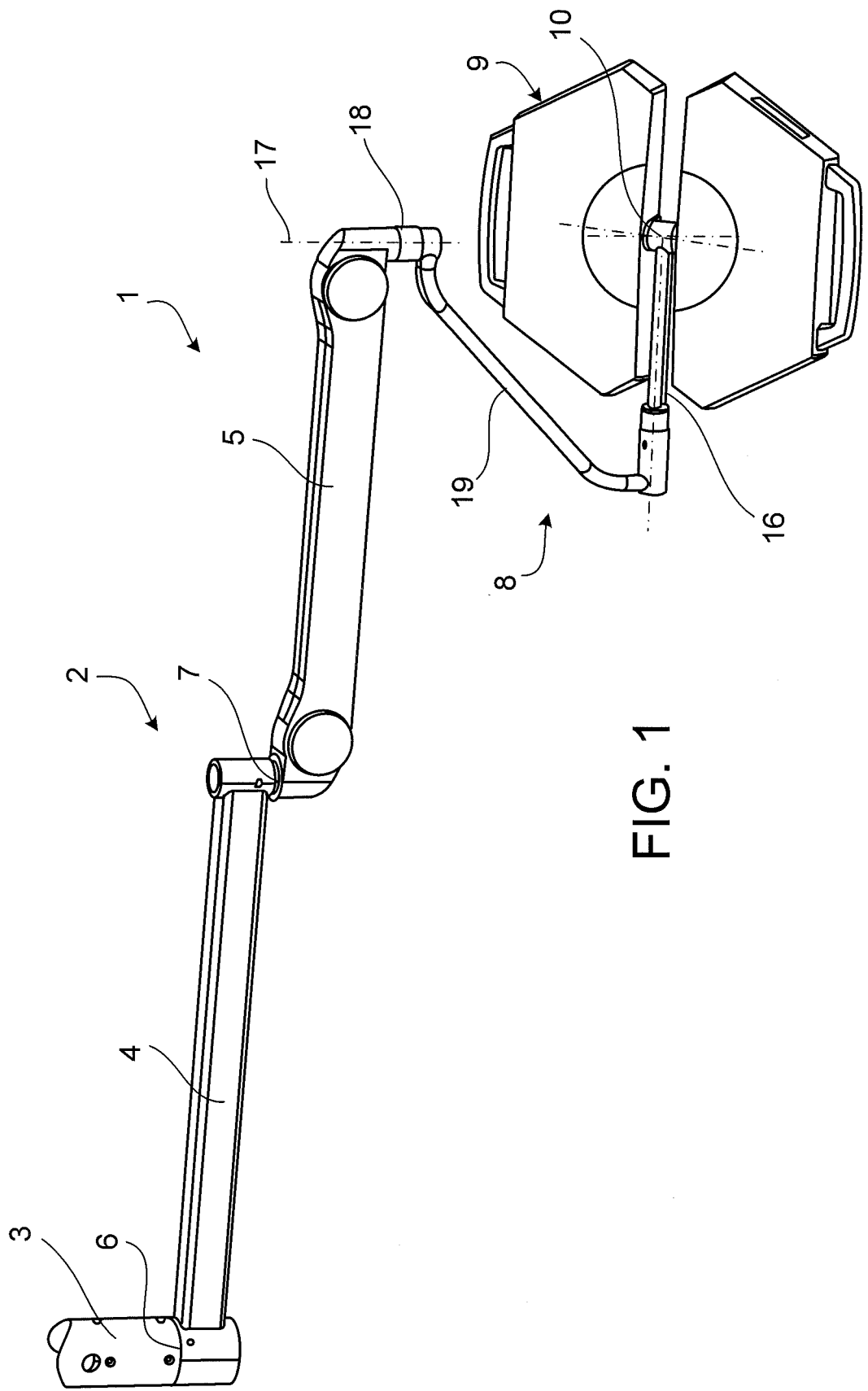
FIG. 1 is an isometric view of a surgical lamp.

FIG. 1 is an isometric view of a surgical lamp 1 that includes a carrying system 2 including a central shaft 3, a first boom 4 that is pivotable around a vertical axis, and a second boom 5 that also is pivotable around the vertical axis and is height-adjustable. The first boom 4 is connected to the central shaft 3 via a pivot joint 6. The second boom 5 is connected to the first boom 4 via a pivot joint 7. The carrying system is attached to a room ceiling, a wall, or a movable stand. The carrying system 2 is connected to a suspension system 8 via a pivot joint 18 having a vertical pivot axis 17.

The carrying system 2 is provided with an electrical supply and control line coming from a supply system via the central shaft 3, the first boom 4, and the second boom 5 for supplying electrical power to and controlling the surgical lamp 1. The pivot joints 6, 7 are typically designed without any stopper so that the booms 4, 5 can be pivoted in any desired angle. Known sliding contacts which are connected with the respective cable portions are mounted in the pivot joints to avoid destroying a full-length cable.

Figure 2:
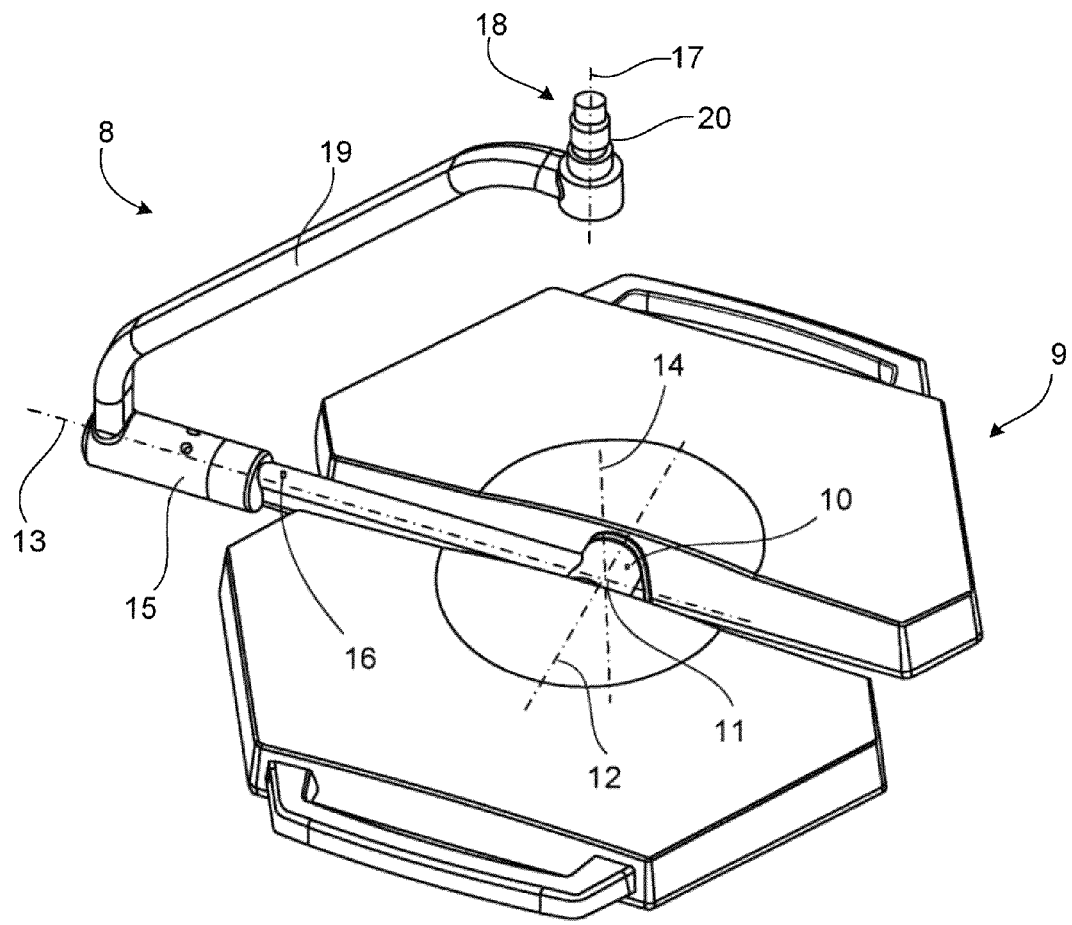
FIG. 2 is an isometric view of a lamp body and a suspension system having first, second, and third pivot joints.

FIG. 2 is an isometric view of a lamp body 9 that is connected to the suspension system 8 of the surgical lamp 1. The suspension system 8 includes a first pivot joint 10 at which an intersection point 11 of a first pivot axis 12 and second pivot axis 13 of a second pivot joint 15 is located. The first pivot axis 12 is perpendicular to the second pivot axis 13. The intersection point 11 is located in the central area of a lamp body 9 and is located on a central axis 14 of the lamp body 9 in this embodiment. The first pivot axis 12 represents the axis of the first pivot joint 10, and the second pivot axis 13 represents the axis of the second pivot joint 15. In this embodiment, a third vertical axis 17 is arranged perpendicular to the second pivot axis 13. However, in certain embodiments, the angle between the third vertical axis 17 and the second pivot axis 13 can be smaller than 90°. In such embodiments, the pivot joint 13 is not oriented in a horizontal plane. Instead, the pivot joint 15 is displaced upwards, in a circular arc around the pivot axis 12 with respect to the first pivot joint 10 and the third pivot joint 18. This arrangement can provide increased head room for the surgical personnel.

The below described first pivot joint 10 is connected to the second pivot joint 15 via a connection element 16. The connection element 16 is formed of a linear, hollow steel member and is connected to the joints by welding. The inner cross section of the steel member is chosen in such way that the required electrical lines can be passed through one or more lumens therein. The cross section of the steel member is dimensioned in such a way that the moment of inertia of an area is able to withstand the bending moment caused by the weight force of the lamp body 9 and the movement force, including the safety factors.

The second pivot joint 15 is connected to the third pivot joint 18 via a second connection element 19. This second connection element 19 is also formed of a hollow steel member. The dimension and the design of the steel member are subject to the same requirements as for the hollow steel member of the first connection element 16. The joints also are welded to the member.

The shape of the connection element 19 is chosen in such way that the design is space-saving and material-saving. Under consideration of the pinch point hazard, the vertical dimension of the connection element 19 is as small as possible in order to install the lamp body 9 as high as possible and to gain head room for the surgical personal. The horizontal dimension of the connection element 19 is chosen in such way that the intersection point 11 is located on the third pivot axis 17 under consideration of the dimensions of the first pivot joint 10, the second pivot joint 15, and the connection element 19.

The connection between the suspension system 8 and the carrying system 2 is achieved via the third pivot joint 18. A journal 20 thereby is introduced into a cylindrical counterpart and secured by a half-moon key. Thus, a pivotable but axially rigid connection is realized. As an alternative embodiment, the pivot joint 18 can be replaced by a stiff connection.

In the second and third pivot joint 15, 18, optionally, the moving forces are reduced by using rolling bearings. In cases in which rolling bearings are used, the joints can be provided with adjustable friction breaks for avoiding a self-actuating shift of the lamp body 9.

The running of the electrical lines through the connection elements 16, 19 and pivot joints 15, 18 is carried out by means of cables in the connection elements 16, 19 and sliding contacts in the pivot joints 15, 18.

Figure 3:
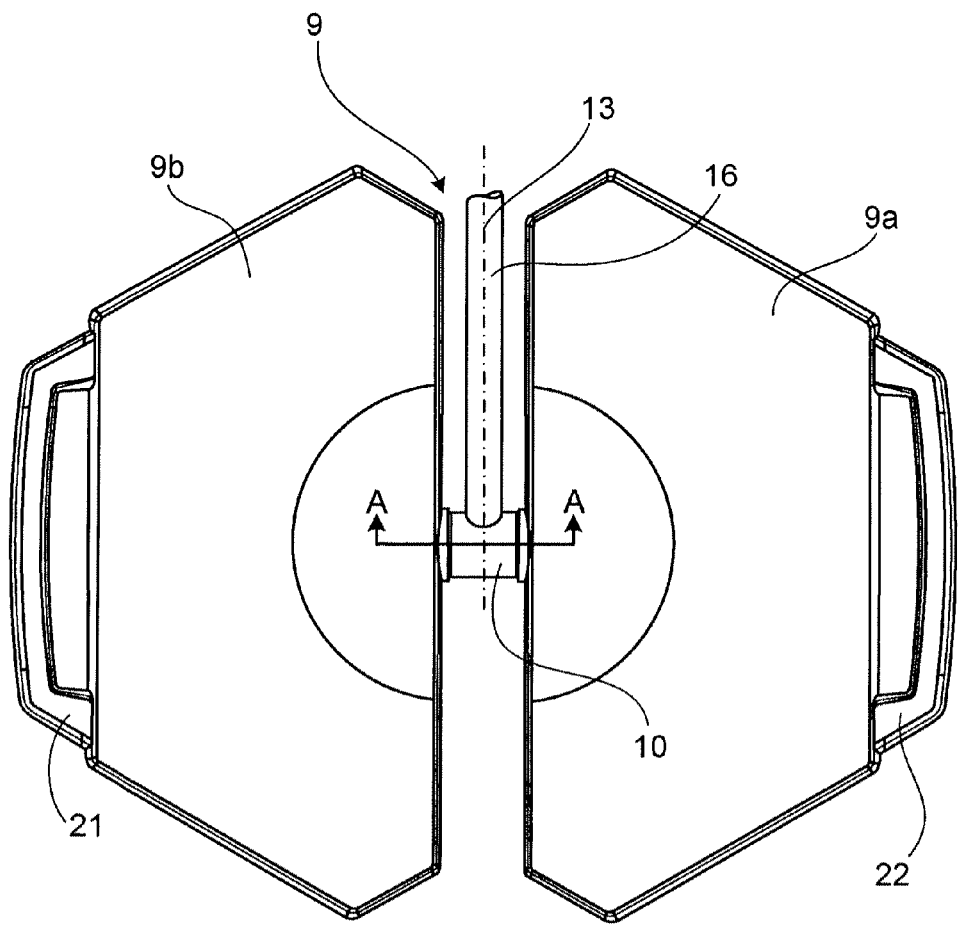
FIG. 3 is a plan view of the lamp body and the first pivot joint of the suspension system.

In FIG. 3, a plan view of the lamp body 9 and the first pivot joint 10 of the suspension system 8 is shown. The lamp body 9 is made up of two halves (one half 9a and one half 9b), which are connected to one another in a torque-proof manner. Thus, the pivoting movement of one of the halves, which can be carried out using its associated handle 21, 22, is transmitted to the other half and, therefore, the orientation of both of the halves 9a and 9b is always the same. The lamp body 9 is non-sterilely positioned by an operator by means of the handle 21, the handle 22, and a third handle (not shown), which is orientated in such a way that the emitted light is directed to the operation field. For positioning and orientating by the sterile surgeon, a further handle (not shown) can be provided.

Figure 4:
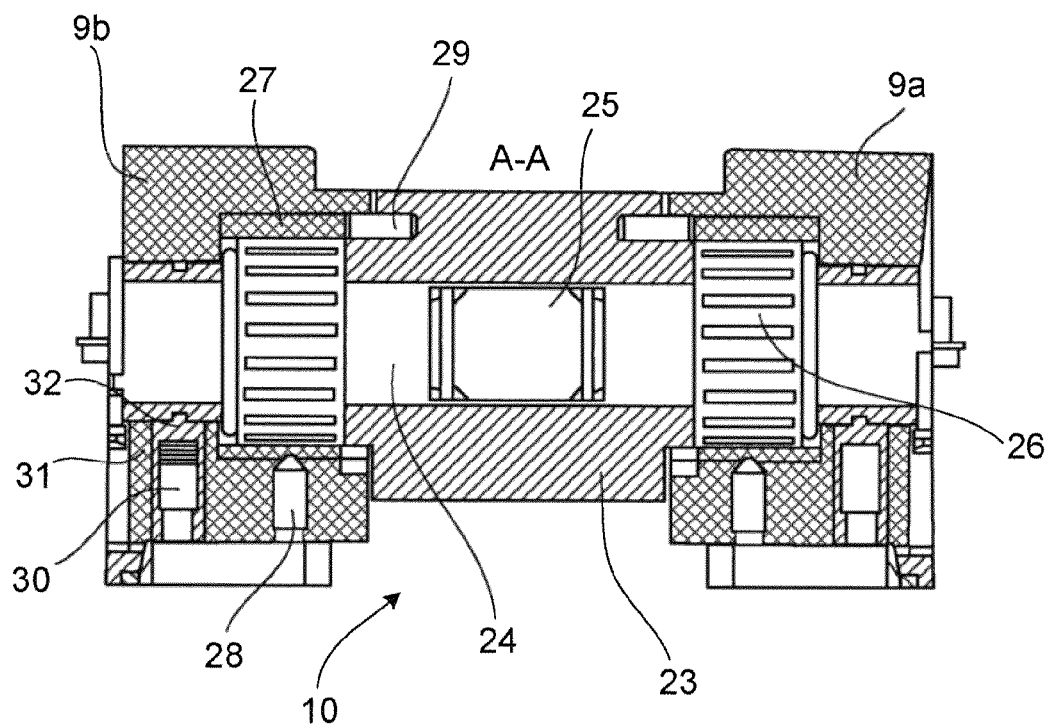
FIG. 4 is a sectional view of the first pivot joint.

FIG. 4 is a sectional view A-A of the first pivot joint 10, having a section course as shown in FIG. 3. The pivot joint 10 includes a hollow shaft 23 that is connected to the connection element 16 by welding. The shaft 23 is provided with an orifice 25 having dimensions similar to the dimensions of the inner free section of the connection element 16 and is aligned with the latter.

Two needle-roller bearings 26 are provided on the shaft 23. At their outer diameter, the needle-roller bearings 26 are surrounded by a bushing 27. The bushings 27 have a flat section with a conical countersinking, which is visible in the sectional plane, at their outer circumference. The bushings 27 and thus the outer rings of the needle-roller bearings 26 are fixed by a screw 28 having a conical tip.

A stopper, which prevents a spinning of the lamp body around the first pivot axis 12, is formed by a pin 29 that is pressed in the shaft 23. A counter part, which is not shown, is attached to the halves 9a, 9b of the lamp body 9 so that a clearance having a sufficient size remains between the handle and the connection element 16 in order to avoid pinching of the user's hand.

A break system consisting of a setscrew 30, a plate spring package 31, and a brake pad 32, which is secured against twisting by the engagement of a tongue in a circumferential groove in the shaft 23 and applies a breaking force, is provided in both halves 9a and 9b of the lamp body 9 (here only shown in the half 9b), radial to the shaft 23.

Cables of the supply and control lines of the lamp body 9 are laid through the free inner section of the connection element 16 and the orifice 25 and in a bore 24 of the shaft 23, and from there guided into the halves 9a and 9b. The electrical connection of both of the halves 9a and 9b is also completed by cables through the bore 24 of the shaft 23. Sliding contacts are not generally necessary here, because stoppers that prevent spinning of the lamp body are provided.

Light sources for emitting light downwards to the operation field, and control devices and supply devices for the light sources are attached in both of the halves 9a and 9b of the lamp body 9.

Other embodiments are within the scope of the following claims.

What is claimed is:

1. A surgical lamp comprising:
a lamp body having a central axis and comprising first and second members that comprise light sources, the first and second members being spaced apart from one another to define a central opening therebetween;
a carrying system; and
a suspension system connecting the lamp body to the carrying system, the suspension system comprising first and second pivot joints and a first connection element,
wherein the first pivot joint is connected to the lamp body within the central opening of the lamp body, the first pivot joint has a first pivot axis that is perpendicular to the central axis, the first pivot axis intersects the central axis within the central opening of the lamp body where the first pivot joint is connected to the lamp body, the second pivot joint has a second pivot axis that is perpendicular to the first pivot axis, an intersection point of the first pivot axis and the second pivot axis is located at the first pivot joint within the central opening of the lamp body, and the lamp body is pivotable around the first pivot axis, and
wherein the first connection element is connected at a first end to the first pivot joint within the central opening of the lamp body and connected at a second end to the second pivot joint.

2. The surgical lamp of claim 1, wherein the first pivot axis and the second pivot axis intersect at a center of gravity of the lamp body.

3. The surgical lamp of claim 2, wherein the first pivot axis and the second pivot axis intersect at a fixed location relative to the lamp body.

4. The surgical lamp of claim 1, wherein the first connection element is configured such that the lamp body can freely rotate relative to the first connection element.

5. The surgical lamp of claim 4, wherein the opening is sized to receive the first connection element of the suspension system when the lamp body is rotated relative to the first connection element.

6. The surgical lamp of claim 5, wherein the first and second members are connected to one another via the first pivot joint, and the first and second members of the lamp body cooperate to define the recess.

7. The surgical lamp of claim 1, wherein the first connection element has a linear shape.

8. The surgical lamp of claim 1, wherein the suspension system further comprises a third pivot joint having a third pivot axis that is vertically orientated and forms a maximum angle of 90° with the second pivot axis.

9. The surgical lamp of claim 8, wherein the suspension system further comprises a second connection element between the second pivot joint and the third pivot joint, the second connection element being configured to allow the lamp body to rotate.

10. The surgical lamp of claim 9, wherein the second connection element is arc-shaped.

11. The surgical lamp of claim 9, wherein the second connection element comprises at least two portions arranged at an angle of less than 180° relative to one another.

12. The surgical lamp of claim 1, wherein the first and second members respectively comprise first and second handles for manipulating the lamp body.

* * * * *